(12) United States Patent
Jin et al.

(10) Patent No.: US 9,812,635 B2
(45) Date of Patent: Nov. 7, 2017

(54) METHOD OF MANUFACTURING ULTRASOUND PROBE

(71) Applicant: SAMSUNG MEDISON CO., LTD., Gangwon-Do (JP)

(72) Inventors: Gil-ju Jin, Gangwon-do (KR); Jung-lim Park, Gangwon-do (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 192 days.

(21) Appl. No.: 14/607,884

(22) Filed: Jan. 28, 2015

(65) Prior Publication Data
US 2015/0250452 A1 Sep. 10, 2015

(30) Foreign Application Priority Data
Mar. 4, 2014 (KR) .................. 10-2014-0025678

(51) Int. Cl.
H01L 41/31 (2013.01)
H01L 41/22 (2013.01)
A61B 8/14 (2006.01)
H01L 41/25 (2013.01)
H01L 41/311 (2013.01)
(Continued)

(52) U.S. Cl.
CPC ............... H01L 41/31 (2013.01); A61B 8/14 (2013.01); A61B 8/4483 (2013.01); B06B 1/0622 (2013.01); H01L 41/22 (2013.01); H01L 41/25 (2013.01); H01L 41/27 (2013.01);
(Continued)

(58) Field of Classification Search
CPC ....... A61B 8/14; A61B 8/4483; B06B 1/0622; H01L 41/22; H01L 41/25; H01L 41/27; H01L 41/29; H01L 41/31; H01L 41/311; Y10T 29/42
See application file for complete search history.

(56) References Cited

U.S. PATENT DOCUMENTS 5,857,974 A    1/1999  Eberle
6,036,647 A *  3/2000  Suorsa ................. Y10T 29/42
                                                      29/25.35
(Continued)

FOREIGN PATENT DOCUMENTS

JP    2006-095178 A    4/2006
JP    4703416 B2       6/2011
(Continued)

OTHER PUBLICATIONS

Extended European Search Report issued in Application No. 15153222.3 dated Aug. 11, 2015.

*Primary Examiner* — A. Dexter Tugbang
(74) *Attorney, Agent, or Firm* — McDermott Will & Emery LLP

(57) ABSTRACT

Provided is a method of manufacturing an ultrasound probe. The method includes: preparing a backing layer having first and second surfaces with different heights due to forming a groove in the backing layer, wherein first and second electrodes are exposed on the first and second surfaces, respectively; forming a third electrode that is in contact with the first electrode; forming a base piezoelectric unit on the third electrode, the base piezoelectric unit including a piezoelectric layer; forming a piezoelectric unit by removing an upper region of the base piezoelectric unit; and forming a fourth electrode on the backing layer and the piezoelectric unit.

18 Claims, 7 Drawing Sheets

(51) Int. Cl.
  *H01L 41/29* (2013.01)
  *B06B 1/06* (2006.01)
  *A61B 8/00* (2006.01)
  *H01L 41/27* (2013.01)

(52) U.S. Cl.
  CPC ............ *H01L 41/29* (2013.01); *H01L 41/311* (2013.01); *Y10T 29/42* (2015.01)

(56) References Cited

U.S. PATENT DOCUMENTS

| | | |
|---|---|---|
| 7,834,522 B2 | 11/2010 | Guo |
| 2008/0033298 A1* | 2/2008 | Habu ..................... Y10T 29/42 600/459 |
| 2008/0312537 A1 | 12/2008 | Hyuga |
| 2009/0204006 A1 | 8/2009 | Wakabayashi et al. |
| 2010/0241003 A1 | 9/2010 | Jung et al. |
| 2010/0241004 A1* | 9/2010 | Jung ..................... B06B 1/0622 600/459 |
| 2014/0154795 A1 | 6/2014 | Lipkens |

FOREIGN PATENT DOCUMENTS

| | | | |
|---|---|---|---|
| JP | 2012182758 A * | 9/2012 | |
| KR | 10-2010-0104534 A | 9/2010 | |
| KR | 10-2010-0104535 A | 9/2010 | |

\* cited by examiner

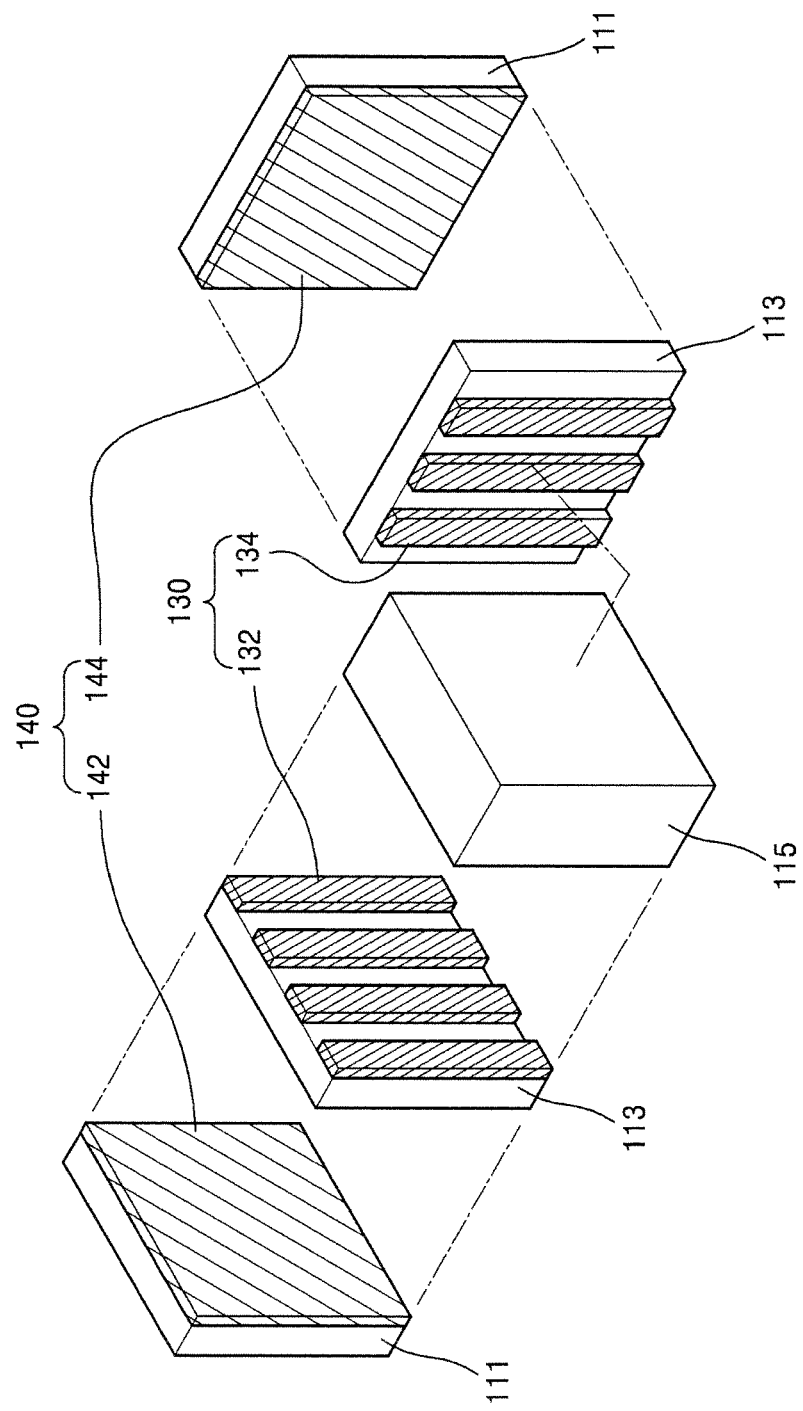

METHOD OF MANUFACTURING ULTRASOUND PROBE

RELATED APPLICATION

This application claims the benefit of Korean Patent Application No. 10-2014-0025678, filed on Mar. 4, 2014, in the Korean Intellectual Property Office, the disclosure of which is incorporated herein in its entirety by reference.

BACKGROUND

1. Field

One or more embodiments of the present invention relate to an ultrasound probe and a method of manufacturing the ultrasound probe.

2. Description of the Related Art

In general, an ultrasound diagnostic apparatus irradiates ultrasounds to an object such as a human being or animal and detects an echo signal reflected from the object to thereby display a tomographic image of tissue on a monitor and provide information necessary for diagnosis of the object. To do so, the ultrasound diagnostic apparatus includes an ultrasound probe for transmitting an ultrasound to the object and receiving an echo signal from the object.

The ultrasound probe has a transducer mounted therein for converting an ultrasound signal into an electrical signal and vice versa. The transducer generally includes a set of a plurality of piezoelectric elements. Thus, the ultrasound diagnostic apparatus having the above-described configuration irradiates an ultrasound to an object, converts a reflected ultrasound echo signal into an electrical signal, and generates an ultrasound image by using the electrical signal.

Such an ultrasound diagnostic apparatus using an ultrasound probe is used for medical purposes such as detection of foreign substances within a living body, measurement of the degree of injury, monitoring of tumors, observation of fetuses, etc.

An ultrasound probe is typically fabricated by manufacturing components thereof separately before assembling them together. However, this assembling method may not only cause a failure in a junction between the components but also make it difficult to reduce the size of the ultrasound probe.

SUMMARY

One or more embodiments of the present invention include an ultrasound probe and a method of manufacturing the ultrasound probe via which a thin piezoelectric layer and a thin matching layer are formed.

Additional aspects will be set forth in part in the description which follows and, in part, will be apparent from the description, or may be learned by practice of the presented embodiments.

According to one or more embodiments of the present invention, a method of manufacturing an ultrasound probe includes: preparing a backing layer having first and second surfaces with different heights due to forming a groove in the backing layer, wherein first and second electrodes are exposed on the first and second surfaces, respectively; forming a third electrode that is in contact with the first electrode; forming a base piezoelectric unit on the third electrode, the base piezoelectric unit including a piezoelectric layer; forming a piezoelectric unit by removing an upper region of the base piezoelectric unit; and forming a fourth electrode on the backing layer and the piezoelectric unit.

The forming of the third electrode may include: forming a conductive material within the groove; and removing a part of the conductive material formed along sidewalls of the groove.

The base piezoelectric unit may be formed by using a joining technique.

A surface of the piezoelectric unit may be at the same level as the second surface.

During the removing of the upper region of the base piezoelectric unit, upper regions of the backing layer and the second electrode may also be removed.

The piezoelectric layer of the piezoelectric unit may contact the fourth electrode.

The base piezoelectric unit may further include a first auxiliary electrode that contacts a top surface of the piezoelectric layer, and the first auxiliary electrode may be removed in the removing of the upper region of the base piezoelectric unit.

The base piezoelectric unit may further include a second auxiliary electrode that contacts a bottom surface of the piezoelectric layer, and the second auxiliary electrode may be in contact with the third electrode in the forming of the base piezoelectric unit.

The piezoelectric layer included in the piezoelectric unit may have a thickness of less than or equal to 200 µm.

The method may further include forming a matching layer on the fourth electrode.

The matching layer may be formed by using at least one of a deposition process and a molding process.

The matching layer may have a thickness of less than or equal to 50 µm.

The third and fourth electrodes may be electrically connected to a chip module substrate for operating the ultrasound probe via first and second electrodes, respectively.

One of the third and fourth electrodes may serve as a ground electrode and the other serves as a signal electrode.

The fourth electrode may be a ground electrode.

The method may further include dicing the third electrode, the piezoelectric unit, and the fourth electrode to form a plurality of third electrode elements, a plurality of piezoelectric elements, and a plurality of fourth electrode elements.

The preparing of the backing layer may include: joining together a first sub-backing layer, the second electrode, a second sub-backing layer, the first electrode, and a third sub-backing layer, all of which are sequentially arranged; and forming the groove by removing portions of the second sub-backing layer, the first electrode, and the third sub-backing layer.

The second sub-backing layer may have a stepped surface.

At least one of the first and second electrodes may be a flexible printed circuit board (PCB).

According to one or more embodiments of the present invention, an ultrasound probe includes: a backing layer having first and second surfaces with different widths due to forming a groove in the backing layer, first and second electrodes disposed within the backing layer and exposed on the first and second surfaces, respectively; a third electrode that is disposed within the groove and contacts the first electrode; a piezoelectric unit that is disposed on the third electrode and includes a piezoelectric layer; and a fourth electrode disposed on the backing layer and the piezoelectric unit.

The piezoelectric unit may further include an auxiliary electrode disposed on a bottom surface of the piezoelectric layer, and a top surface of the piezoelectric layer may contact the fourth electrode, and the auxiliary electrode contacts the third electrode.

BRIEF DESCRIPTION OF THE DRAWINGS

These and/or other aspects will become apparent and more readily appreciated from the following description of the embodiments, taken in conjunction with the accompanying drawings in which:

FIG. 2 is a diagram illustrating a method of manufacturing a backing layer of the ultrasound probe of FIG. 1, which includes first and second electrodes, according to an exemplary embodiment of the present invention;

DETAILED DESCRIPTION

Figure 1:
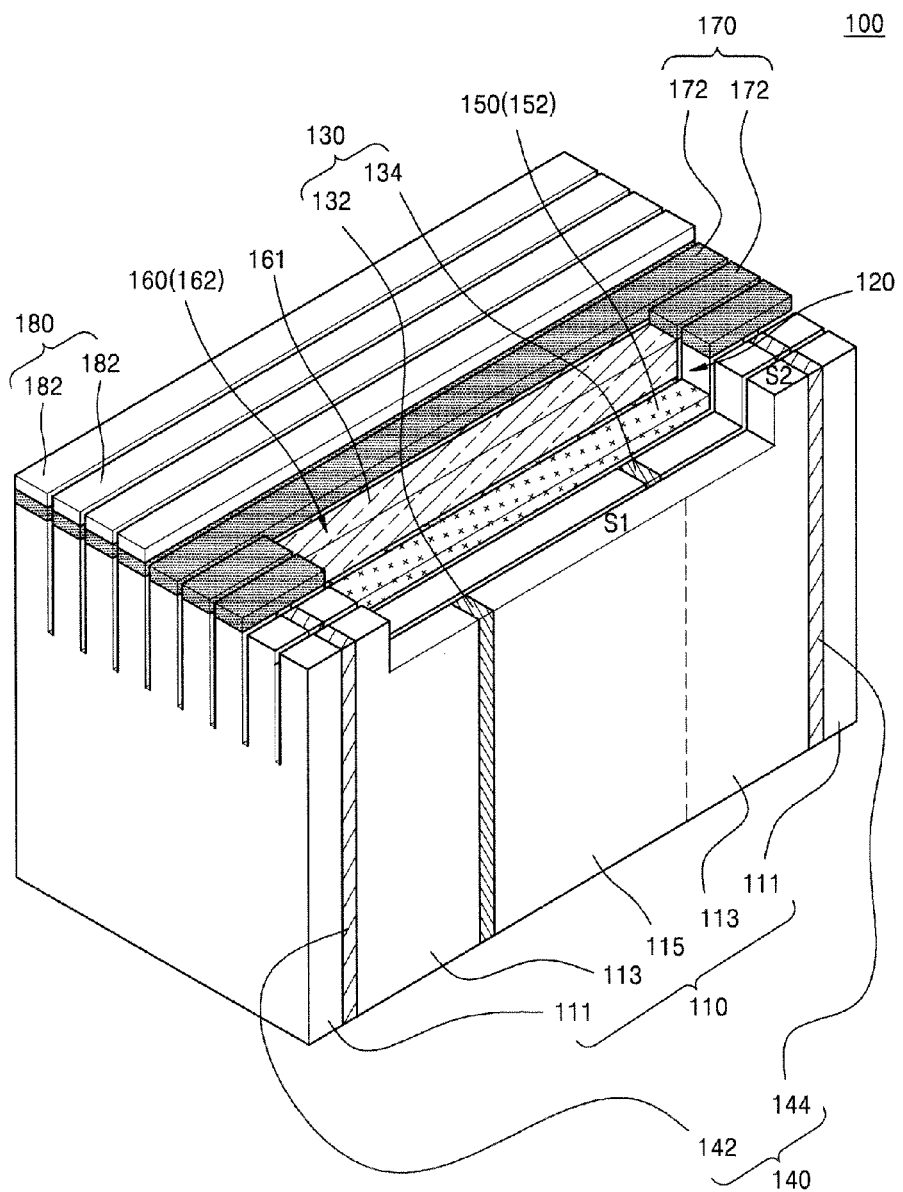
FIG. 1 is a schematic diagram of a configuration of an ultrasound probe according to an exemplary embodiment of the present invention.

Exemplary embodiments will now be described more fully hereinafter with reference to the accompanying drawings. In the drawings, reference numerals refer to like elements throughout, and repeated descriptions thereof are omitted here.

In the present specification, an "object" may include a person or an animal, or a part of a person or an animal. For example, the object may include organs such as the liver, the heart, the womb, the brain, a breast, and the abdomen, or a blood vessel. Furthermore, a "user" refers to a medical professional, such as a doctor, a nurse, a medical laboratory technologist, a medical imaging expert, and an engineer who repairs a medical apparatus, but the user is not limited thereto. Expressions such as "at least one of," when preceding a list of elements, modify the entire list of elements and do not modify the individual elements of the list.

FIG. 1 is a schematic diagram of a configuration of an ultrasound probe 100 according to an exemplary embodiment of the present invention. Referring to FIG. 1, the ultrasound probe 100 includes a backing layer 110 having first and second surfaces S1 and S2 with different heights due to forming a groove 120 in the backing layer 110, a first electrode 130 that is disposed inside the backing layer 110 and exposed on the first surface S1, a second electrode 140 that is disposed inside the backing layer 110 and exposed on the second surface S2, a third electrode 150 that is disposed in the groove 120 and contacts the first electrode 130, a piezoelectric unit 160 that includes a piezoelectric layer 161 and is disposed on the third electrode 150, and a fourth electrode 170 disposed on the backing layer 110 and the piezoelectric unit 160. The ultrasound probe 100 may further include a matching layer 180 formed on the fourth electrode 170.

The backing layer 110 may absorb ultrasounds transmitted thereinto and has the groove 120 formed therein. The groove 120 may be formed in a top surface of the backing layer 110 so that the groove 120 has a shape corresponding to that of the piezoelectric unit 160 and is concave in the backing layer 110. Thus, the backing layer 110 may have first and second surfaces S1 and S2 having different heights. Furthermore, the backing layer 110 may be formed of a material containing rubber with epoxy resin and tungsten powder added thereto.

The backing layer 110 may be formed by joining together a plurality of sub-backing layers, e.g., first through third sub-backing layers 111, 113, and 115. For example, the second sub-backing layers 113 are disposed on either edge of the third sub-backing layer 115, and the first sub-backing layers 111 are respectively disposed on edges of the second sub-backing layers 113.

The second electrodes 140 may be disposed between the first and second sub-backing layers 111 and 113, and the first electrode 130 may be disposed between the second and third sub-backing layers 113 and 115. Each of the first and second electrodes 130 and 140 has one end exposed on a top of the backing layer 110 and the other end exposed on a bottom of the backing layer 110. Therefore, the ends of the and second electrodes 130 and 140 on one side of each of the first and the second electrodes 130 and 140 are in contact with other electrodes disposed on the backing layer 110, e.g., the third and fourth electrodes 150 and 170, respectively. The ends of the first and second electrodes 130 and 140 on the other side thereof are electrically connected to a chip module substrate (not shown?) of the ultrasound probe 100. Although only the first and second electrodes 130 and 140 are disposed between the second sub-backing layer 113 and either the third or first sub-backing layer 115 or 111, embodiments of the present invention are not limited thereto. For example, the first and second electrodes 130 and 140 may be disposed on insulating layers, respectively, and the insulating layers having the first and second electrodes 130 and 140 thereon may be disposed between each of the first through third sub-backing layers 111, 113, and 115.

One of the first and second electrodes 130 and 140 may receive a driving signal from the chip module substrate while the other may receive a ground signal therefrom. For example, the first and second electrodes 130 and 140 may receive a driving signal and a ground signal from the chip module substrate, respectively. In this case, the first and second electrodes 130 and 140 may also be called a signal electrode and a ground electrode, respectively. The first and second electrodes 130 and 140 are hereinafter referred to as a signal electrode and a ground electrode, respectively, but are not limited thereto. For example, a ground signal and a driving signal may be applied to the first and second electrodes 130 and 140, respectively.

The first electrode 130 serving as a signal electrode may include a plurality of first electrode elements 132 and 134 that are separate from each other so that one of the first electrode elements 132 and 134 may contact one of a plurality of piezoelectric elements, as described below. The second electrode 140 serving as a ground electrode may include a plurality of second electrode elements (142 and 144?) that are separate from each other, and each second electrode element 142 or 144 may be formed of a single conductive material layer.

Referring to FIG. 1, each of the first and second electrodes 130 and 140 may include (two types of electrode elements 132 and 134 (or 142 and 144). The first electrode elements 132 and 134 are disposed on the left and right sides of the third sub-backing layer 115, respectively, and in a staggered form. This staggered arrangement may decrease the size of a piezoelectric element. Furthermore, since the second electrode 140 includes the two second electrode elements 142 and 144, one of the second electrode elements 142 and 144 may receive a ground signal even if the other electrode element suffers from a ground failure. Thus, a failure rate of the ultrasound probe 100 may be reduced. To achieve this, the first and second electrodes 130 and 140 each may include one type of electrode elements.

At least one of the first and second electrodes 130 and 140 may be a flexible printed circuit board (PCB).

The third electrode 150 is disposed in the groove 120 and contacts the first electrode 130. Thus, when the first electrode 130 serves as a signal electrode, the third electrode 150 may be a signal electrode as well. The third electrode 150 may include a plurality of third electrode elements 152 that are separate from each other. Since the third electrode 150 is formed using a deposition process such as sputtering, the third electrode 150 may be thin. For example, the third electrode 150 may have a thickness of about 7000 Å.

The piezoelectric unit 160 is disposed within the groove 120 and on the third electrode 150. The piezoelectric unit 160 may also include a plurality of separate piezoelectric elements 162 that are in contact with the third electrode elements 152, respectively. Thus, the piezoelectric elements 162 convert electrical signals into ultrasounds and vice versa while oscillating. The piezoelectric unit 160 may be made of a material that causes a piezoelectric phenomenon to occur. The material may include at least one of zinc oxide (ZnO), aluminum nitride (AlN), lead zirconate titanate ($PbZrTiO_3$; PZT), lead lanthanum zirconate titanate ($PbLaZrTiO_3$; PLZT), barium titanate ($BaTiO_3$; BT), lead titanate ($PbTiO_3$; PT), and lead magnesium niobate ($Pb(Mg_{1/3}Nb_{2/3})O_3$—PT (PMN—PT). The third electrode 150 and the piezoelectric unit 160 may be formed in the groove 120 by using a deposition process. Since the piezoelectric unit is formed by using a deposition method, the piezoelectric layer 161 may have a thickness of less than or equal to 200 μm.

The piezoelectric unit 160 may only include the piezoelectric layer 161 made of a piezoelectric material. If the piezoelectric unit 160 only includes the piezoelectric layer 161, a bottom surface and a top surface of the piezoelectric layer 161 may contact the third and fourth electrodes 150 and 170, respectively, but are not limited thereto. The piezoelectric unit 160 may further include an auxiliary electrode (not shown) that contacts the bottom surface of the piezoelectric layer 161. The auxiliary electrode may contact the third electrode 150 as well. In other words, by joining the auxiliary electrode directly with the third electrode 150, a separation between the piezoelectric unit 160 and the third electrode 150 may be reduced, and accordingly, a failure rate of the ultrasound probe 100 may be reduced.

The fourth electrode 170 is disposed on the backing layer 110 and the piezoelectric unit 160 and is electrically connected to the piezoelectric unit 160 and the second electrode 140. For example, the fourth electrode 170 may contact the piezoelectric unit 160 and the second electrode 140 for electrical connection. Like the first through third electrodes 130, 140, and 150, the fourth electrode 170 may include a plurality of fourth electrode elements 172 that are separate from one another. Each of the fourth electrode elements 172 is disposed on regions of the piezoelectric element 162 and the backing layer 110 and is electrically connected to the second electrode 140. For example, each of the fourth electrode elements 172 may contact the second electrode 140 for electrical connection. A surface of the piezoelectric unit 160 may be at the same level as the second surface S2 of the backing layer 110. The fourth electrode 170 may be formed by using a deposition process such as sputtering, vacuum evaporation, vapor deposition, plating, silk screen, printing. Since the fourth electrode 170 is formed using a deposition process, the fourth electrode 170 may be thin. For example, the fourth electrode 170 may have a thickness of about 7000 Å.

The first through fourth electrodes 130, 140, 150, and 170 may be formed of conductive materials. Examples of the conductive materials may include metals, carbon nanostructures such as carbon nanotubes (CNTs) and graphene, various conductive polymers such as polypyrrole, polyaniline, polyacetylene, polythiophene, polyphnylene vinylene, polyphenylene sulfide, poly p-phenylene, and polyheterocycle vinylene, metal oxides such as indium tin oxide (ITO), aluminum zinc oxide (AZO), indium zinc oxide (IZO), tin oxide ($SnO_2$), or indium oxide ($In_2O_3$), and thin-films with dispersed metal nanoparticles including Al, copper (Cu), gold (Au), and silver (Ag).

The matching layer 180 may match an acoustic impedance of an ultrasound generated by the piezoelectric unit 160 to an acoustic impedance of an object. The matching layer 180 may gradually change the acoustic impedance of the ultrasound so that it is close to that of the object. The matching layer 180 may also include a plurality of matching elements 182 disposed on the fourth electrode elements 172, respectively, but is not limited thereto. The matching layer 180 may be formed of a single layer or have a multi-layer structure. Since the matching layer 180 may also be formed using a deposition process, the matching layer 180 may have a thickness of less than or equal to 50 μm. The matching layer 180 may be formed by using a molding process and then a polishing process.

The ultrasound probe 100 may further include an acoustic lens (not shown) for condensing ultrasounds. The acoustic lens is used to focus ultrasounds generated by the piezoelectric unit 160. The acoustic lens may be formed of a material such as silicon rubber having acoustic impedance that is close to that of an object. In addition, the acoustic lens may have a convex or flat central portion. The acoustic lens may have various shapes according to design requirements.

FIG. 2 is a diagram illustrating a method of manufacturing the backing layer 110 in the ultrasound probe 100 of FIG. 1, which includes the first and second electrodes 130 and 140, according to an exemplary embodiment of the present invention. Referring to FIG. 2, the second electrode 140 may be formed on a side of the first sub-backing layer 111 by depositing a conductive material. In this case, the second electrode 140 may be formed as a pattern by partitioning the conductive material into the plurality of second electrode elements 142 and 144, or as a single electrode layer. Then, the first electrode 130 may be formed on a side of the second sub-backing layer 113. The first electrode 130 may be patterned into the plurality of first electrode elements 132 and 134 by depositing a conductive material and then patterning the same. Thereafter, the second sub-backing layer 113 with the first electrode 130 formed on the side thereof may be joined to a side of the third sub-backing layer 115, and the first sub-backing layer 111 having the second electrode 140 on the side thereof may be bonded to a side of the second sub-backing layer 113. The first through third sub-backing layers 111, 113, and 115 may be joined to one another simultaneously or in a different order than described above. Empty spaces between the second sub-backing layer 113 and either the first or third sub-backing layer 111 or 115 may be filled with backing materials during joining of the first through third sub-backing layers 111, 113, and 115. The first and second electrodes 130 and 140 may be flexible PCBs.

FIGS. 3A through 3I are reference diagrams for explaining a method of manufacturing the ultrasound probe 100 of FIG. 1 by using the backing layer 110 shown in FIG. 2, according to an exemplary embodiment of the present invention.

Figure 3A:
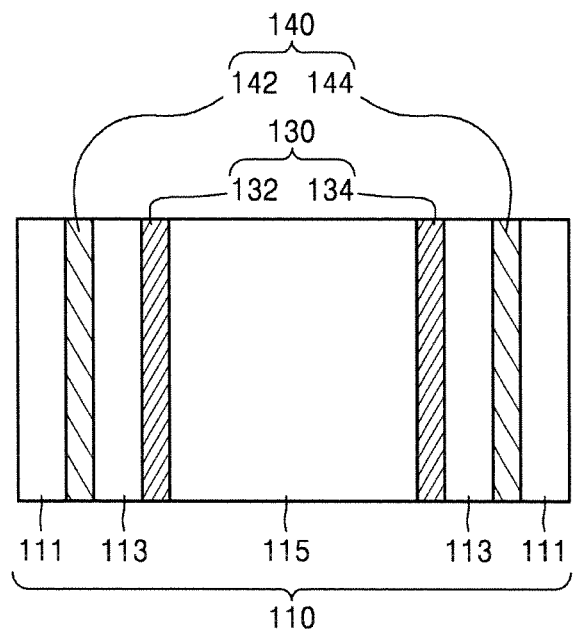
FIGS. 3A through 3I are diagrams for explaining a method of manufacturing the ultrasound probe of FIG. 1 by using the backing layer shown in FIG. 2, according to an exemplary embodiment of the present invention.

FIG. 3A illustrates the result of joining the first through third sub-backing layers 111, 113, and 115 shown in FIG. 2. As shown in FIG. 3A, the first through third sub-backing layers 111, 113, and 115 may be joined together to form the backing layer 110 including the first and second electrodes 130 and 140

Figure 3B:
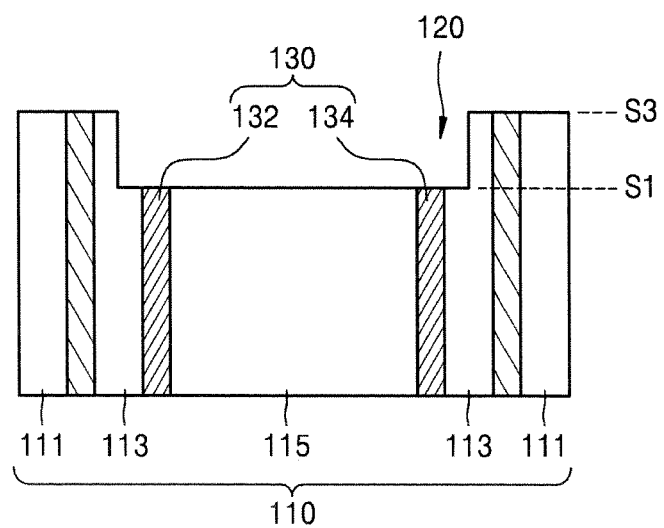

Referring to FIG. 3B, the groove 120 is formed in an upper portion of the backing layer 110 by removing a portion of the second sub-backing layer 113 and the third sub-backing layer 115. The removal process may include an etching or polishing process. Thus, the second sub-backing layer 113 may have a stepped surface. By forming the groove 120, the backing layer 110 may have first and third surfaces S1 and S3 with different heights. The first and second electrodes 130 and 140 may be exposed on the first and third surfaces S1 and S3, respectively.

Figure 3C:
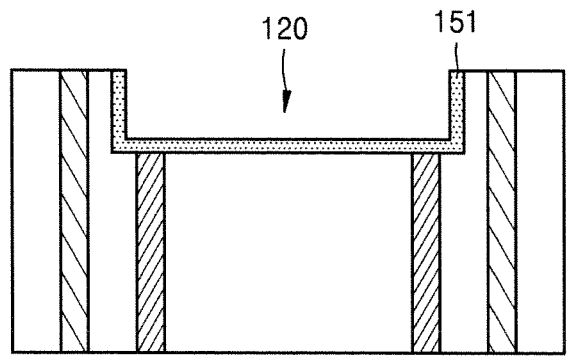

Referring to FIG. 3C, a conductive material 151 may be formed in the groove 120 by using sputtering. Examples of the conductive material 151 may include metals, carbon nanostructures such as CNTs and graphene, various conductive polymers such as polypyrrole, polyaniline, polyacetylene, polythiophene, polyphenylene vinylene, polyphenylene sulfide, poly p-phenylene, and polyheterocycle vinylene, metal oxides such as ITO, AZO, IZO, $SnO_2$, or $In_2O_3$, and thin-films with dispersed metal nanoparticles including Al, Cu, Au, and Ag.

Figure 3D:
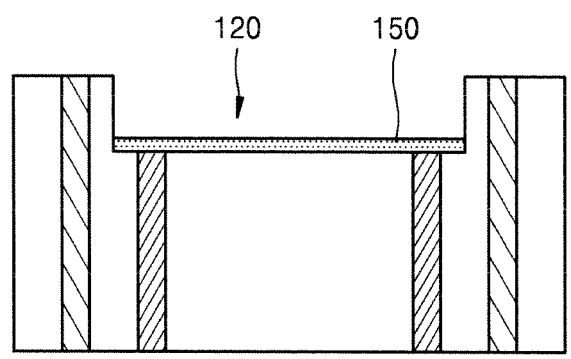

Referring to FIG. 3D, the third electrode 150 may be formed by removing a part of the conductive material 151 formed along sidewalls of the groove 120. For example, the third electrode 150 may be formed by etching or cutting the part of the conductive material 151. The third electrode 150 may be formed on a bottom surface of the groove 120 and electrically connected to the first electrode 130. For example, the third electrode 150 may contact the first electrode 130 for electrical connection.

Figure 3E:
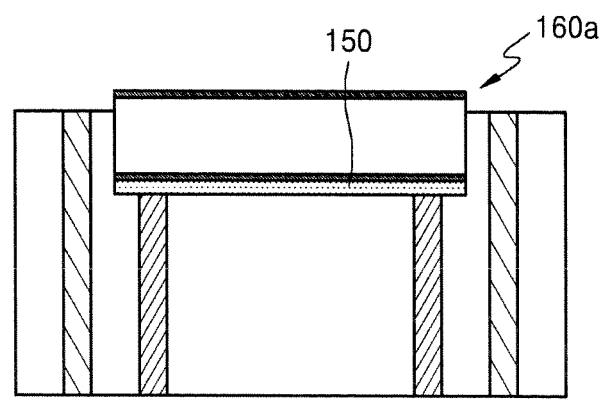

Referring to FIG. 3E, a base piezoelectric unit 160a may be formed in the groove 120 and include the piezoelectric layer 161. The base piezoelectric unit 160a may further include first and second auxiliary electrodes (163 and 164 in FIG. 4D) disposed on top and bottom surfaces of the piezoelectric layer 161, respectively.

FIGS. 4A through 4D illustrate the base piezoelectric unit 160a shown in FIG. 3E according to exemplary embodiments of the present invention.

Figure 4A:
FIGS. 4A through 4D illustrate a base piezoelectric element shown in FIG. 3E according to exemplary embodiments of the present invention.
Figure 4B:
Figure 4C:
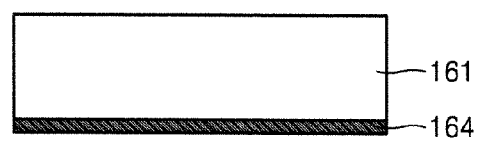
Figure 4D:

As shown in FIG. 4A, the base piezoelectric unit 160a may only include the piezoelectric layer 161, but is not limited thereto. As shown in FIG. 4B, the base piezoelectric unit 160a may further include the first auxiliary electrode 163 disposed on the top surface of the piezoelectric layer 161. Referring to FIG. 4C, the base piezoelectric unit 160a may further include the second auxiliary electrode 164 disposed on the bottom surface of the piezoelectric layer 161. Referring to FIG. 4D, the base piezoelectric unit 160a may further include the first and second auxiliary electrodes 163 and 164 disposed on the top and bottom surfaces of the piezoelectric layer 161, respectively. Referring back to FIG. 3E, the base piezoelectric unit 160a, including the piezoelectric layer 161 and the first and second auxiliary electrodes 163 and 164, is formed in the groove 120.

Figure 3F:
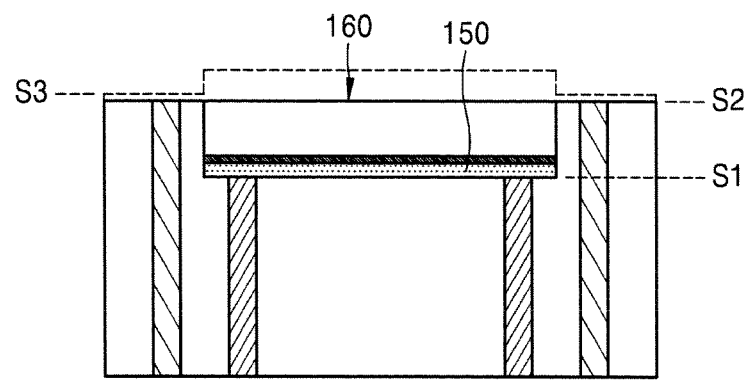

Then, referring to FIG. 3F, an upper portion of the base piezoelectric unit 160a is removed to form the piezoelectric unit 160. By removing the upper portion of the base piezoelectric unit 160a, a surface of the piezoelectric unit 160 is at the same level as a second surface S2 of the backing layer 110. During removal of the upper portion of the base piezoelectric unit 160a, an upper portion of the piezoelectric layer 161 may be removed as well. Since the piezoelectric unit 160 is formed by removing part of the base piezoelectric unit 160a, a thickness of the piezoelectric layer 161 may be adjusted regardless of a depth of the groove 120. The upper portion of the base piezoelectric unit 160a may be removed using an etching or polishing process.

Furthermore, by simultaneously removing the backing layer 110, the second electrode 140, and the base piezoelectric unit 160a, the resulting structure may have equal height at a time so that the fourth electrode 170 is formed thereon.

Figure 3G:
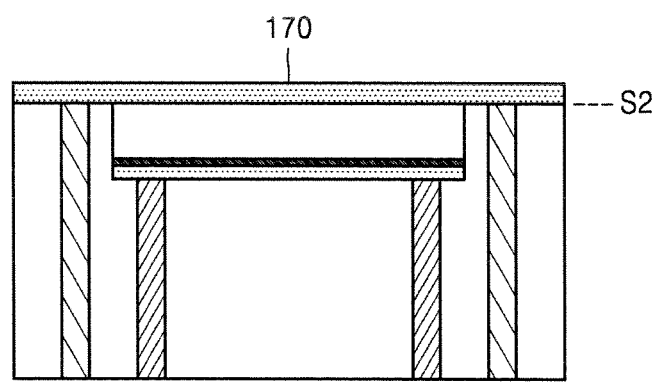

Referring to FIG. 3G, the fourth electrode 170 may then be formed on the second surface S2 of the backing layer 110 and the piezoelectric unit 160. The fourth electrode 170 may also be formed by depositing a conductive material thereon. The fourth electrode 170 may contact the piezoelectric unit 160 as well as the second electrode 140 exposed on the second surface S2. Thus, the fourth electrode 170 may ground a top surface of the piezoelectric unit 160 in response to a ground signal applied through the second electrode 140.

Figure 3H:
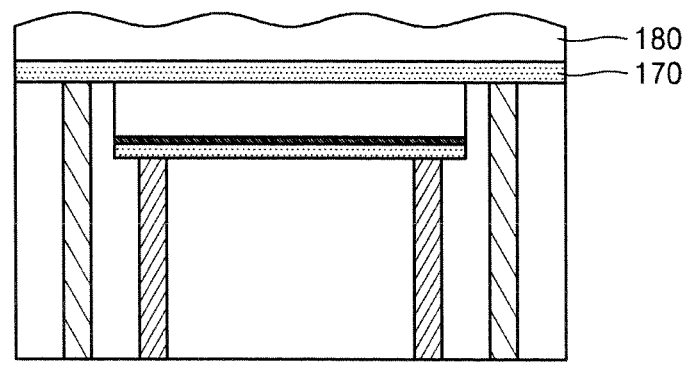
Figure 3I:
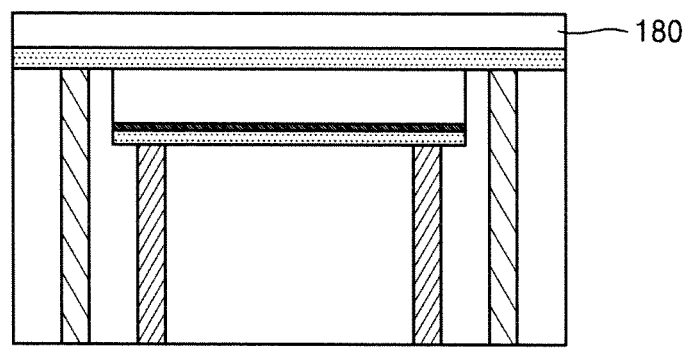

Furthermore, referring to FIG. 3H, the matching layer 180 may be formed on the fourth electrode 170 by using a deposition process such as sputtering, vacuum evaporation, vapor deposition, plating, silk screen, printing. Since the matching layer 180 is formed by using a deposition process, the matching layer 180 may be a thin layer having a thickness of less than or equal to 50 μm. However, embodiments of the present invention are not limited thereto. The matching layer 180 may also be formed by using a molding process. Then, as shown in FIG. 3I, the matching layer 180 may be planarized by using an etching or polishing process.

Subsequently, the matching layer 180, the fourth electrode 170, the piezoelectric unit 160, the third electrode 150, and a portion of the backing layer 110 may be diced to form the plurality of matching elements 182, the plurality of fourth electrode elements 172, the plurality of piezoelectric elements 162, and the plurality of third electrode elements 152, as shown in FIG. 1. Although not shown in FIG. 1, an acoustic lens may be stacked on the matching elements 182.

Figure 5:
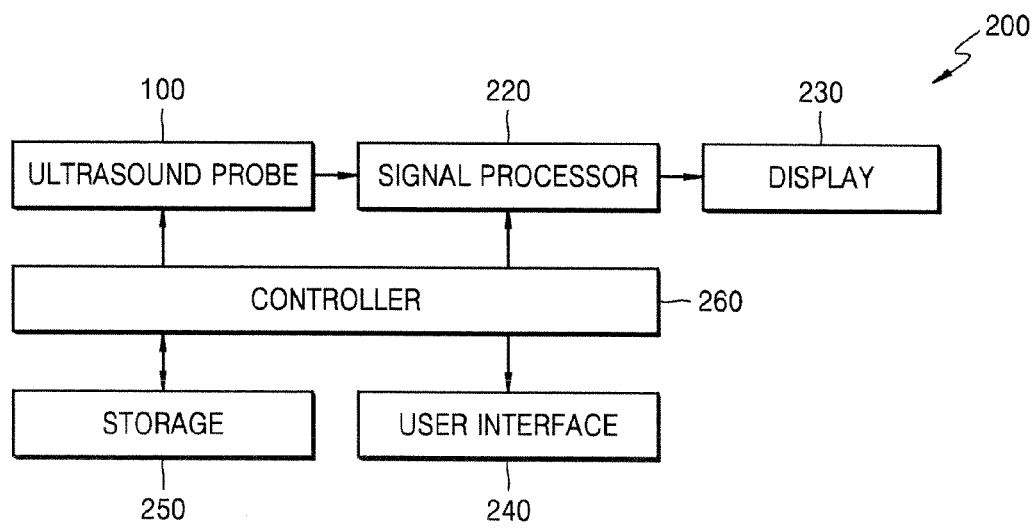
FIG. 5 is a block diagram of an ultrasound diagnostic apparatus including the ultrasound probe of FIG. 1.

FIG. 5 is a block diagram of an ultrasound diagnostic apparatus 200 including the ultrasound probe 100 of FIG. 1. Referring to FIG. 5, the ultrasound diagnostic apparatus 200 includes the ultrasound probe 100 for transmitting or receiving ultrasounds, a signal processor 220 that processes a signal applied by the ultrasound probe 100 to generate an image, a display 230 for displaying an image, a user interface 240 for receiving a user command, a storage 250 for storing various types of information, and a controller 260 for controlling overall operations of the ultrasound diagnostic apparatus 200.

The ultrasound probe 100 is configured to transmit an ultrasound to an object and receive an ultrasound echo signal reflected from the object, which will be described in more detail below.

The signal processor 220 may process ultrasound data generated by the ultrasound probe 100 and generate an ultrasound image. For example, the ultrasound image may be at least one of a brightness (B) mode image indicating the intensity of an ultrasound echo signal reflected from an object as brightness, a Doppler mode image showing a moving object as a spectrum by using a Doppler effect, a motion (M) mode image showing movement of an object at a predetermined position over time, an elasticity mode image indicating a difference between deformations of an object when compression is applied and when no compression is applied, and a color (C) mode image representing the speed of a moving object in color by using a Doppler effect. Since an ultrasound image may be generated by using a currently implementable method, a detailed description thereof is omitted herein. In addition, according to an embodiment of the present invention, the ultrasound image may include images of all dimensions, such as one-dimensional (1D), two-dimensional (2D), three-dimensional (3D), and four-dimensional (4D) images.

The display 230 displays information that is processed by the ultrasound diagnostic apparatus 200. For example, the display 230 may display an ultrasound image generated by the signal processor 220 as well as a graphical user interface (GUI) for requesting a user input.

The display 230 may include at least one of a liquid crystal display (LCD), a thin film transistor-LCD (TFT-LCD), an organic light-emitting diode (OLED) display, a flexible display, a 3D display, and an electrophoretic display. The ultrasound diagnostic apparatus 200 may include two or more displays according to embodiments of the present invention.

The user interface 240 is a means via which a user inputs data for controlling the ultrasound diagnostic apparatus 200. The user interlace 240 may include a keypad, a mouse, a touch panel, and a trackball. However, the user interface 240 is not limited thereto and may further include various other input elements such as a jog wheel, jog switch, etc.

The touch panel may detect both a real touch where a pointer actually touches a screen and a proximity touch where the pointer approaches the screen while being separate from the screen by less than a predetermined distance. In the present specification, the term 'pointer' means a tool for touching a particular portion on or near the touch panel. Examples of the pointer may include a stylus pen and a body part such as fingers.

In addition, the touch panel may be realized as a touch screen that forms a layer structure with the display 230. The touch screen may be implemented as various types such as capacitive overlay, resistive overlay, infrared beam, surface acoustic wave, integral strain gauge, and piezoelectric touch screens. The touch screen is very useful because it functions as both the display 230 and the user interface 240.

Although not shown in FIG. 5, various sensors may be disposed within or near the touch panel so as to sense a touch. A tactile sensor is an example of the sensors for sensing a touch. The tactile sensor is used to sense a touch of a particular object to the same or greater degree than the degree to which a human can sense the touch. The tactile sensor may detect various types of information including the roughness of a contact surface, the hardness of an object to be touched, and the temperature of a point to be touched.

A proximity sensor is another example of the sensors for sensing a touch. The proximity sensor means a sensor that senses the presence of an object that is approaching or is located near a predetermined detection surface by using the force of an electromagnetic field or infrared light without any mechanical contact. Examples of the proximity sensor include a transmissive photoelectric sensor, a direct reflective photoelectric sensor, a mirror reflective photoelectric sensor, a high-frequency oscillation proximity sensor, a capacitive proximity sensor, a magnetic proximity sensor, and an infrared proximity sensor.

The storage 250 stores various types of information that are processed by the ultrasound diagnostic apparatus 200. For example, the storage 250 may store medical data related to diagnosis of an object, such as images, and algorithms or programs that are executed in the ultrasound diagnostic apparatus 200.

The storage 250 may include at least one storage medium from among a flash memory-type storage medium, a hard disk-type storage medium, a multimedia card micro-type storage medium, card-type memories (e.g., an SD memory, an XD memory, and the like), Random Access Memory (RAM), Static Random Access Memory (SRAM), Read-Only Memory (ROM), Electrically Erasable Programmable ROM (EEPROM), PROM, magnetic memory, a magnetic disc, and an optical disc. The ultrasound diagnostic apparatus 200 may utilize a web storage or a cloud server that functions as the storage 250 online.

The controller 260 controls the overall operations of the ultrasound diagnostic apparatus 200. In detail, the controller 260 may control operations of the ultrasound probe 100, the signal processor 220, and the display 230. For example, the controller 260 may control the signal processor 220 to generate an image by using a user command received via the user interface 240 or programs stored in the storage 250. The controller 260 may also control the display 230 to display the image generated by the signal processor 220.

As described above, according to the one or more of the above embodiments of the present invention, it is possible to form a thin piezoelectric unit and a thin matching layer. In addition, a failure rate may be reduced during the manufacture of an ultrasound probe.

While one or more embodiments of the present invention have been described with reference to the figures, it should be understood that the exemplary embodiments described therein should be considered in a descriptive sense only and not for purposes of limitation. Thus, it will be understood by those of ordinary skill in the art that various changes in form and details may be made therein without departing from the spirit and scope of the present invention as defined by the following claims. All modifications and substitutions within the scope of the appended claims and their equivalents will be construed as being included in the present invention.

What is claimed is:

1. A method of manufacturing an ultrasound probe, the method comprising:
   preparing a backing layer having first and second surfaces with different heights due to forming a groove in the backing layer, wherein first and second electrodes are exposed on the first and second surfaces of the backing layer, respectively;
   forming a third electrode that is in contact with the first electrode;
   forming a base piezoelectric unit on the third electrode, the base piezoelectric unit including a piezoelectric layer;
   forming a piezoelectric unit by removing an upper region of the base piezoelectric unit such that an upper surface of the piezoelectric unit is at a same level as the second surface of the backing layer; and
   forming a fourth electrode on the second surface of the backing layer and the upper surface of the piezoelectric unit.

2. The method of claim 1, wherein the forming of the third electrode comprises:
   forming a conductive material within the groove; and
   removing a part of the conductive material formed along sidewalls of the groove.

3. The method of claim 1, wherein the base piezoelectric unit is formed by using a joining technique.

4. The method of claim 1, wherein during the removing of the upper region of the base piezoelectric unit, upper regions of the backing layer and the second electrode are also removed.

5. The method of claim 1, wherein the piezoelectric layer of the piezoelectric unit contacts the fourth electrode.

6. The method of claim 1, wherein the base piezoelectric unit further comprises a first auxiliary electrode that contacts a top surface of the piezoelectric layer, and
wherein the first auxiliary electrode is removed in the removing of the upper region of the base piezoelectric unit.

7. The method of claim 1, wherein the base piezoelectric unit further comprises a second auxiliary electrode that contacts a bottom surface of the piezoelectric layer, and
wherein the second auxiliary electrode is in contact with the third electrode in the forming of the base piezoelectric unit.

8. The method of claim 1, wherein the piezoelectric layer included in the piezoelectric unit has a thickness of less than or equal to 200 μm.

9. The method of claim 1, further comprising forming a matching layer on the fourth electrode.

10. The method of claim 9, wherein the matching layer is formed by using at least one of a deposition process and a molding process.

11. The method of claim 9, wherein the matching layer has a thickness of less than or equal to 50 μm.

12. The method of claim 1, wherein the third and fourth electrodes are electrically connected to a chip module substrate for operating the ultrasound probe via first and second electrodes, respectively.

13. The method of claim 1, wherein one of the third and fourth electrodes serves as a ground electrode and the other serves as a signal electrode.

14. The method of claim 13, wherein the fourth electrode is a ground electrode.

15. The method of claim 1, further comprising dicing the third electrode, the piezoelectric unit, and the fourth electrode to form a plurality of third electrode elements, a plurality of piezoelectric elements, and a plurality of fourth electrode elements.

16. The method of claim 1, wherein the preparing of the backing layer comprises:
joining together a first sub-backing layer, the second electrode, a second sub-backing layer, the first electrode, and a third sub-backing layer, all of which are sequentially arranged; and
forming the groove by removing portions of the second sub-backing layer, the first electrode, and the third sub-backing layer.

17. The method of claim 16, wherein the second sub-backing layer has a stepped surface.

18. The method of claim 1, wherein at least one of the first and second electrodes is a flexible printed circuit board (PCB).

* * * * *